under the Bon Patent Cooperation Treaty

(12) United States Patent
Doht

(10) Patent No.: US 6,958,157 B1
(45) Date of Patent: Oct. 25, 2005

(54) TRIIODOMETHANE THICKENER CONJUGATES, A METHOD FOR THEIR PRODUCTION AND THEIR USE AS DISINFECTANT CLEANERS AND HYGIENE PRODUCTS

(76) Inventor: Ulrich Doht, Steinmerderweg 2, 21147 Hamburg (DE)

( * ) Notice: Subject to any disclaimer, the term of this patent is extended or adjusted under 35 U.S.C. 154(b) by 354 days.

(21) Appl. No.: 10/130,940

(22) PCT Filed: Nov. 25, 2000

(86) PCT No.: PCT/EP00/11738

§ 371 (c)(1),
(2), (4) Date: May 24, 2002

(87) PCT Pub. No.: WO01/37822

PCT Pub. Date: May 31, 2001

(30) Foreign Application Priority Data

Nov. 25, 1999 (DE) ................................ 199 57 918

(51) Int. Cl.[7] ........................ A01N 25/00; A01K 29/00
(52) U.S. Cl. ..................... 424/405; 119/603; 119/650; 119/652; 119/653; 514/938; 514/941; 514/943
(58) Field of Search ................................ 424/488, 358, 424/47, 59, 78, 79, 405; 514/341, 406, 407, 514/943, 938, 941; 119/600, 603, 650, 652, 119/653

(56) References Cited

U.S. PATENT DOCUMENTS 4,478,853 A * 10/1984 Chaussee ..................... 514/772
5,456,745 A * 10/1995 Roreger et al. .......... 106/140.1
5,503,847 A * 4/1996 Queen et al. ................ 424/488

FOREIGN PATENT DOCUMENTS

| EP | 244118 | 11/1987 |
|---|---|---|
| EP | 258761 A | 3/1988 |
| EP | 487066 A | 5/1992 |
| GB | 2048070 A | 12/1980 |
| JP | 02 953649 B | 9/1999 |
| WO | 96/40086 | 12/1996 |

* cited by examiner

Primary Examiner—Thurman K. Page
Assistant Examiner—Micah-Paul Young
(74) Attorney, Agent, or Firm—Levy & Grandinetti

(57) ABSTRACT

The invention relates to a new conjugate, based on triiodomethane, which also contains at least one natural organic and/or modified natural organic and/or inorganic thickener. Cellulose ethers or starch ethers are particularly suitable for use as the thickener. Said conjugate can be used as a disinfectant and can be introduced into ointments or creams. As a hydrogel containing water and a solvent in addition to the conjugate, with a viscosity of between 5,000 and 400,000 mPa*s (20° C.), preferably between 10,000 and 30,000 wPa*s (20° C.), the product is extremely suitable for use as a disinfectant cleaner and hygiene product for cleaning and maintaining animal horn for example of horses, cattle and sheep. In addition, the hydrogel can contain at least one polyalcohol, in particular glycerine. According to one production method, a hydrogel is produced from water and a thickener and the polyalcohol is fast added thereto at a temperature of between 20 and 60° C., followed by the solvent containing the triiodomethane.

15 Claims, No Drawings

TRIIODOMETHANE THICKENER CONJUGATES, A METHOD FOR THEIR PRODUCTION AND THEIR USE AS DISINFECTANT CLEANERS AND HYGIENE PRODUCTS

This application is the U.S. National Phase of PCT Application Number PCT/EP00/11738, filed on Nov. 25, 2000, which claims priority to German Application Number 199 57 918.3, filed Nov. 25, 1999.

DESCRIPTION

The invention relates to a conjugate of triiodomethane and water thickeners, a hydrogel containing this conjugate, the use of these compounds and a process for their production.

Certain iodine compounds containing iodine in the oxidation state 0 or −1 are known to act microbicidally. Accordingly, such compounds are used in disinfecting agents. Elemental iodine, mostly in the form of a polyvinylpyrrolidone conjugate, has been established for example very successfully as antiseptic for wound dressing. The care of horns for farmyard animals, in particular of horses, cattle and sheep, requires still further measures in addition to disinfecting agents. The horn of the hoof soles (integumentary appendage) of these animals requires care with moisture-binding agents, since untreated horn has the tendency to form cracks, and loses elasticity significantly. Horn-disintegrating faecal bacteria may severely penetrate into the hoof sole via these cracks and horn gaps.

These horn-disintegrating enteric bacteria (*Fusobacterii necrophori*) accumulate together with ichor in the barn base (straw or wood shavings) and increase there under anaerobic conditions and attack the animal hoof. It is thus known in the care and cleaning of animal hooves to treat them with ointments based on zinc oxide. In the case of severe attack of the hoof soles, they are best controlled externally using antibacterially effective agents. Generally known agents for this are, for example 1–5% strength hydrogen peroxide, 5–10% copper (II) compounds or 1.5% strength formaldehyde in water or alcohols. The hitherto most effective available agent is 4–10% strength triiodomethane in diethyl ether (see "Richtlinien für Reiten and Fahren [Guidelines for riding and running]", $2^{nd}$ Edition, Volume VI (Horse ownership), page 128, FN Verlag, Warendorf 1980). Conventionally however, hydrophilic conditions in effective disinfecting agents are necessary for effective fighting of bacteria.

Anaerobic bacteria are also suitable to also degenerate other organic macromolecules (for example cellulose ethers) in addition to polypeptides (hoof horn). Hydrogen peroxide, formaldehyde copper (II)-ammonia complexes and zinc chloride are known for degradation, crosslinking and complexing reactions with organic thickeners (for example cellulose ethers).

From human medicine, an average viscosity, water-miscible iodine adsorbate with polyvinylpyrrolidone (PVP) is known as antiseptic (for example Betaisodona®). Polyvinylpyrrolidone is designated as a fully synthetic organic thickening agent. However, this agent has serious disadvantages, which make it unsuitable for use as a hoof care agent. Thus, firstly the high price should be mentioned. Furthermore, Betaisodona® has the disadvantage of liquefying at body temperature. Use within the framework of farmyard animal ownership is thus not suitable, since when using the product on animal hooves or claws, the said liquefaction starts immediately, so that the agent does not adhere to the applied point. Furthermore, the supply of moisture within the framework of hoof care is of central significance. Betaisodona® does not contain enough water by far in order to be able to adequately supply the animal hoof. However, simple premixing of additional water is not possible, since the product would then become fluid and could no longer guarantee simple application.

Modified natural organic thickeners are often used as gel formers for thin alcohol-containing (rapidly drying) gels, which leave behind films with disinfectant action on the skin due to a low microbicide content. In EP 0 640 352, ethyl cellulose is used, other cellulose ethers are likewise suitable for this (WO 99/43205). In addition to iodine or iodophores, such as PVP or iodine-starch complexes, other antimicrobially acting substances may also be used.

All agents known hitherto for the care or disinfection of hoof soles have considerable disadvantages. Hence, they have too low viscosity in particular, can be handled only with difficulty and have inadequate effectiveness due to lack of adhesive effect. A product sold under the name "Chevaline-Strahlpflegepaste" consists of bolus alba and isopropanol and contains as active ingredient an organic copper (II) compound. However, this product is not homogeneous and has a rather brittle consistency. It can therefore only be applied with difficulty. Furthermore, it has the serious disadvantage that copper salts harden horn according to experience. The basically very effective triiodomethane in diethyl ether on the other hand is not only difficult to handle due to the high volatility, but in addition is not without danger because of flammability. The proportioning is also very difficult due to the volatility, and rapid application cannot be guaranteed.

On the whole, iodine compounds have proved to be particularly effective microbicides in disinfecting agents. However, the hitherto known compounds have the serious disadvantages mentioned for the field of application of horn care of animal hooves.

The object of the present invention therefore consists in providing an iodine compound, in particular in conjunction with cleaning and care agents, which has an antibacterial action, is simple to handle and may be applied rapidly and exactly. Furthermore, it should have good adhesive capacity and adequate water solubility.

In context with the invention, surprisingly it has been found that triiodomethane forms conjugates with thickeners, preferably with inorganic and organic, in particular with natural organic and modified natural organic thickeners. Furthermore, they fulfill the requirements mentioned. In contrast to all hitherto known compounds, the thickeners thus act not only as gel former in water, but also as complex former for the triiodomethane.

Modified natural organic macromolecules, such as cellulose ether or starch ether, are preferably used as thickeners. Methylcellulose, ethylcellulose, methylhydroxyethylcellulose, methylhydroxypropylcellulose, hydroxyethylcellulose, hydroxypropylcellulose, ethylhydroxyethylcellulose, carboxymethylcellulose, hydroxypropyl starch ether, hydroxyethyl starch ether or carboxymethyl starch ether are preferably used, wherein methylcellulose, methylhydroxypropylcellulose, carboxymethylcellulose and hydroxypropyl starch ether are particularly suitable.

Natural organic macromolecules, such as commercially available foodstuff products are also particularly suitable as thickeners, preferably agar-agar, guar meal, locust tree meal and starch, wherein locust tree meal is particularly suitable.

Inorganic macromolecules, such as for example commercially available polysilicic acids or clay minerals, preferably bentonite, are likewise well suited.

The conjugate of the invention has excellent suitability for introduction into ointments, creams, gels and pastes. As such, it is particularly suitable for the use as effective disinfectant cleaner for cleaning and care of warm-blooded animals, in particular as horn care agent for horse hooves and claws in cattle and sheep. In such a form, it is appropriate to the tasks placed on the invention: It is simple to handle and may be applied precisely and rapidly. The microbicide thus acts antibacterially not only on the horn to be treated, but also excludes bacterial impurities, which are unavoidably mixed into the disinfectant cleaner due to application during hoof care.

In particular the compounds of cellulose ethers and triiodomethane have proved to be very suitable agents for horn care of warm-blooded animals, firstly in the form of an ointment or cream containing the above-mentioned conjugate, secondly, in the form of hydrogels.

The conjugate of the invention is thus advantageously present in a hydrogel, which additionally contains water and a solubility promoter and has a viscosity between 5,000 and 400,000 mPa*s (20° C.), preferably between 10,000 and 30,000 mPa*s (20° C.). Preferred solubility promoters are glycol ethers, in particular monomethyl, monoethyl, monobutyl, dimethyl, diethyl or dibutyl ether of ethylene glycol, diethylene glycol, triethylene glycol, propylene glycol, dipropylene glycol or tripropylene glycol, in particular dipropylene glycol-mono-methyl ether or dipropylene glycoldimethyl ether. The proportion of water-soluble solubility promoter is preferably 0.5 to 30 wt. %, in particular 2 to 10wt. %, based on the gel of the invention.

The proportion of modified organic thickener is preferably 0.5 to 20 wt. %, in particular 1 to 15 wt. %, based on the gel of the invention. The proportion of natural organic thickener is preferably 0.3 to 15 wt. %, in particular 0.5 to 10 wt. %, based on the gel of the invention. The proportion of inorganic thickener is preferably 5 to 25 wt. %, in particular 10 to 20 wt. %, based on the gel of the invention.

The proportion of triiodomethane is preferably 0.01 to 20 wt. %, in particular 0.1 to 15 wt. %, based on the gel of the invention.

It is of considerable significance for hoof care to protect the hoof from drying out. The gel should therefore have a high retention capacity for water for its application as disinfectant cleaner for cleaning and care of horn in order to counteract drying out.

In a particularly advantageous embodiment, the gel of the invention therefore also has at least one polyalcohol, preferably ethylene glycol, diethylene glycol, triethylene glycol, 1,2-propylene glycol, dipropylene glycol, tripropylene glycol and glycerol, wherein diethylene glycol, dipropylene glycol and glycerol are particularly suitable. The proportion of polyalcohols is preferably 0.01 to 40 wt. %, in particular 5 to 30 wt. %, based on the gel of the invention.

The gel may be adjusted to be very malleable by the addition of glycerol. In addition, glycerol additionally increases the water-retaining capacity of the gel, so that the substance is particularly suitable as a care agent. This is important and not provided in hitherto known disinfecting agents, for example triiodomethane in diethyl ether.

The latter compound evaporates very easily, that is dries rapidly, and effects drying out of the horn. However, it does not ensure that water is retained in the horn in order to impart malleability to it. The gel of the invention on the other hand dries only very slowly and may thus unfold a particular care effect.

The gel of the invention may also contain additives, such as other care components from the group of long-chain esters, preferably triglycerides, in particular laurel oil (*Lauri Oleum*). The proportion of additives is preferably 1 to 10 wt,%, in particular 3 to 8 wt. %, based on the gel of the invention. Perfume oils may also be added to the gel. The proportion of such perfume oils is preferably 0.01 to 0.1 wt.%.

Furthermore, the present invention also relates to a process for producing such hydrogels. First of all a highly viscous hydrogel is thus produced in conventional manner.

The water temperature to be maintained depends on the type of thickener used. To this solution are then added at 20–60° C. in the following sequence with intensive stirring, first of all the polyalcohol and then in some of the solubility promoter, the microbicide, triiodomethane. Homogenisation then advantageously takes place at a temperature of 20–40° C., preferably at room temperature.

The conjugates, which the triiodomethane forms with the thickeners, may be precipitated at high sodium chloride concentration and/or high water dilution. Dilutions of the gels of the invention have been tested with up to 12 times the quantity of water at 0%, 5% and 10% sodium chloride addition. Cellulose ethers and starches are thus particularly suitable as thickeners.

The gels of the invention show excellent adhesive properties due to their viscosity and very good effectiveness as disinfectant cleaner on horn of animal hooves, as have not been achieved by hitherto known agents. They may be taken up for the required area of application without further auxiliaries using a brush and placed simply in horn gaps of animal hooves. Drying out of the horn is prevented in sustained manner by the water retention of the thickening agent used and horn already softened is clearly stabilised again. At the same time, during application with a brush, surface-active thickening agents act as non-ionic surfactants (foam formation). Astoundingly, already after three to five times application in the stream furrows, even stream rot expansion on horse hooves may thus be stopped. Bacterial barn impurities, which are brought into the gel due to frequent use, do not reduce the viscosity of the gel.

The gel of the invention may also be used in other, for example general medical fields of application. Use in skin treatment and in the wound dressing should thus be mentioned in particular.

Further advantages, embodiments and application possibilities can be seen from the examples mentioned below.

Hydrogels of different composition have been produced. The substances used can be seen in Table 1 below. In a comparative test, instead of an inorganic, a natural organic or a modified natural organic thickener, a fully synthetic organic thickener was selected. Glycerol was used as polyalcohol. Dipropylene glycol-dimethyl ether and dipropylene glycol-monomethyl ether were used as solubility promoter. The production of the highly viscous hydrogels is effected by generally known methods. The water temperatures to be maintained depend on the type of thickener used and are likewise listed in Table 1 below.

The further components are then added to the thickener solutions at 20–60° C. with intensive stirring in the following sequence:

a) polyalcohol
b) solubility promoter (dipropylene glycol-dimethyl ether and/or dipropylene glycol-monomethyl ether)
c) microbicide.

The microbicide is added dissolved in some of the glycol ether to be used. It is advantageously then homogenised at room temperature. The gels of the invention have viscosities from 5,000 to 400,000 mPa*s.

When using triiodomethane with organic thickeners, lemon yellow-coloured aqueous triiodomethane adsorbates (conjugates) are thus always formed. The solutions dry on a glass plate to form transparent films having very high elasticity.

TABLE 1

| Test | Thickener Used | Water temperature | Thickener | Water | Glycerol | Dipropylene glycol-dimethyl ether | Dipropylene glycol-mono-methyl ether | Triiodomethane | Thyme oil | Tea-tree oil |
|---|---|---|---|---|---|---|---|---|---|---|
| | Inorganic thickener | | | | | | | | | |
| #1 | Bentonite (e.g. from Messrs. Caelo, #4095) | 20° C. | 15% | 61% | 16% | 0% | 7% | 0,6% | 0% | 0% |
| | Natural organic thickeners | | | | | | | | | |
| #2 | Lotus tree meal (Foodstuff quality) | 100° C. | 2% | 76% | 13% | 0% | 8% | 0,6% | 0% | 0% |
| #3 | Potato starch (Foodstuff quality) | 100° C. | 8% | 63% | 21% | 0% | 7% | 0,6% | 0% | 0% |
| #4 | Agar-agar (e.g. from Messrs. Caelo, #0003) | 100° C. | 1% | 80% | 11% | 0% | 8% | 0,6% | 0% | 0% |
| | Modified natural organic thickeners | | | | | | | | | |
| #5 | Hydroxypropyl starch (Foodstuff quality) | 20° C. | 11% | 70% | 11% | 0% | 7% | 0,5% | 0% | 0% |
| #6 | Carboxymethylcellulose, Na salt (e.g. from Messrs. Merck #105058) | 20 ° C. | 4% | 73% | 17% | 0% | 6% | 0,5% | 0% | 0% |
| #7 | Hydroxypropyl methylcellulose | 50 ° C. | 2% | 74% | 10% | 0% | 10% | 0,5% | 4,5% | 0% |
| #8 | Hydroxypropyl methylcellulose | 50 ° C. | 2% | 80% | 10% | 0% | 6% | 0,5% | 0% | % |
| #9 | Hydroxypropyl methylcellulose (e.g. from Messrs. Aldrich, #42, 317-3) | 50 ° C. | 1% | 79% | 0% | 19% | 0% | 0,8% | 0% | 0% |
| #10 | Methylcellulose (e.g. from Messrs. Aldrich, #27, 441-0) | 50 ° C. | 9% | 71% | 12% | 0% | 7% | 0,6% | 0% | 0% |
| | Comparative text (fully synthetic organic thickener) | | | | | | | | | |
| #11 | Polyvinylpyrrolidone (e.g. from Messrs. Caelo, #2362) | 20 ° C. | 48% | 31% | 12% | 0% | 8% | 0,7% | 0% | 0% |

It can be seen from the comparative test with polyvinyl pyrrolidone that this is less well suited for the field of use of the invention. In order to achieve a viscosity corresponding to the other products, a considerably higher proportion of thickener is necessary. For this only a maximum of half the water content may be achieved. Since an important aspect of the disinfectant cleaner of the invention is its water content and the care effect associated therewith, it becomes clear that fully synthetic organic thickeners are less suitable for use according to the invention.

A two-month lasting effect of the gel on the hoof horn was tested. Application of the gel does not negatively influence the properties of hoof horn. A freshly cut piece of horn was thus divided and placed in water and in a triiodomethane-containing gel of the invention. After two months the following were assessed: elasticity of the horn, disintegration products, discolouration. The result is shown in Table 2 below:

TABLE 2

| | In gel | In water |
|---|---|---|
| Elasticity of the horn | Unchanged | Brittle |
| Discolouration of the horn | None | Dark |
| Disintegration products | None | Black suspended matter; foul smell of the water |

The production of triiodomethane-thickener conjugates is effected by precipitating the hydrogels produced according to the above exemplary embodiment by means of high sodium chloride concentration and/or high water dilution. The gels of the invention are thus diluted by up to 12 times the quantity of water at 0%, 5% and 10% sodium chloride addition.

The adsorption capacity of the thickeners used with respect to triiodomethane may be assessed from the colour of the solution and from the quantity of uniformly coloured precipitate. Precipitation from a thickener-free solution serves for comparison; a finely disperse lemon-yellow precipitate of triiodomethane and a colourless aqueous phase is thus produced. The result is shown in Table 3 below:

TABLE 3

| Adsorption capacity of the macromolecule | Solubility of the adsorbate (conjugate) | Macromolecule (thickener) |
|---|---|---|
| Poor | — | Polyvinylpyrrolidone |
| | Good | Potato starch |
| Average | Good | Starches (hydroxypropyl-subst.) |
| | Good | Methylcelluloses (hydropropyl- or carboxy-subst.) |

TABLE 3-continued

| Adsorption capacity of the macromolecule | Solubility of the adsorbate (conjugate) | Macromolecule (thickener) |
|---|---|---|
| Average | Average | Methylcellulose |
| Good | Poor | Agar-agar, locust tree meal Bentonite |

At high dilution of the gels of the invention, the conjugates of triiodomethane and various thickeners precipitate in water at up to 10% sodium chloride content as more or less voluminous precipitates. Poor solubility conjugates may already be precipitated by a low water dilution, good solubility conjugates on the other hand only in high water dilution with simultaneous use of sodium chloride.

In contrast to pure triiodomethane, the triiodomethane conjugates have poor solubility in dialkyl ethers, such as for example diethyl ether or methyl tert-butyl ether. The conjugates dry on a glass plate to form a milky-cloudy, brittle film.

The isolated precipitates contain the total triiodomethane quantity in finely disperse distributed form, in addition to changing quantities of thickener and water. These precipitates may be distributed, taking into consideration the water content, simply in commercially available pharmaceutical base materials, for example water-containing hydrophilic ointment (Unguentum emulsificans aquosum; DAB (Deutsches Arzneibuch/German Pharmaceutical Book) 1999), hydrophilic ointment (*Unguentum emulsificans*; DAB 1999), glycerol ointment (*Unguentum glycerine*; DAB 6) or base cream (*Cremor basalis*, DAC (Deutsches Arzneimittelcodex/German Pharmaceutical Codex) 1997). For this voluminous precipitates containing large amounts of water (for example conjugates with agar-agar, methylcellulose, bentonite) are distributed in hydrophilic ointment or glycerol ointment. Compact precipitates (for example conjugates with hydroxypropylmethylcellulose, locust tree meal, starch) may on the other hand also be dispersed in base cream or water-containing hydrophilic ointment. The viscosity may be readjusted using water and/or glycerol. The following Table 4 gives an overview of possible products.

TABLE 4

| Triiodomethane conjugate with | | Ointment or cream base used |
|---|---|---|
| Starch | Compact, low water-content | Water-containing hydrophilic ointment (e.g. from Messrs. Caelo #3106) |
| Methylcellulose | Voluminous, high water content | Hydrophilic ointment (e.g. from Messrs. Caelo #3104) |
| Methylcellulose | Voluminous, high water content | Glycerol ointment (e.g. from Messrs. Caelo #3114) |
| Agar-agar | Voluminous, very high water content | Base cream (e.g. from Messrs. Caelo #3013) |

Triiodomethane conjugates with thickeners may therefore serve quite generally as preservatives in ointments, creams, gels and pastes. In the examples, the triiodomethane content is 0.5% and other horn-care additives, such as for example solid laurel oil (*Oleum Lauri expressum*, DAB 6), may be mixed in. These mixtures are likewise suitable as horn-care agents like the above-mentioned gels.

What is claimed is:

1. A hydrogel comprising:
   a conjugate comprising 0.01 to 20 wt. % triiodomethane; and
   at least one thickener being a modified natural organic thickener selected from the group consisting of cellulose ethers and starch ethers;
   water; and
   a solubility promoter, said solubility promotor is a glycol ether selected from the group consisting of a monomethyl, monoethyl, monobutyl, dimethyl, diethyl or dibutyl ether of ethylene glycol, diethylene glycol, triethylene glycol, propylene glycol, dipropylene glycol or tripropylene glycol, wherein said hydrogel has a viscosity between 5,000 and 400,000 mPa*s (20° C.).

2. A method for treating the hooves or claws of an animal in need of such treatment comprising:
   applying to said hoof or claw a conjugate comprising:
   triiodomethane;
   at least one thickener being a modified natural organic thickener selected from the group consisting of cellulose ethers and starch ethers;
   water; and
   a solubility promoter, said solubility promoter is a glycol ether selected from the group consisting of a monomethyl, monoethyl, monobutyl, dimethyl, diethyl or dibutyl ether of ethylene glycol, diethylene, glycol, triethylene glycol, propylene glycol, dipropylene glycol or tripropylene glycol.

3. A method for treating the hooves or claws of an animal in need of such treatment comprising:
   applying to said hoof or claw a hydrogel comprising a conjugate comprising:
   triiodomethane;
   at least one thickener being a modifies natural organic thickener selected from the group consisting of cellulose ethers and starch ethers;
   water; and
   a solubility promoter, said solubility promoter is a glycol ether selected from the group consisting of a monomethyl, monoethyl, monobutyl, dimethyl, diethyl or dibutyl ether of ethylene glycol, diethylene, glycol, triethylene glycol, propylene glycol, dipropylene glycol or tripropylene glycol, wherein said hydrogel has a viscosity between 5,000 and 400,000 mPa*s (20° C.).

4. The hydrogel of claim 1 wherein the thickener is a natural organic thickener, selected from the group consisting of agar-agar, guar meal, locust tree meal, and starch.

5. The hydrogel of claim 1 wherein the thickener is an inorganic thickener, selected from the group consisting of a polysilicic acid and a clay mineral.

6. The hydrogel of claim 1 wherein the hydrogel contains 0.3 to 25 wt. % thickener, and 0.5 to 30 wt. %, solubility promoter.

7. The hydrogel of claim 1, wherein the hydrogel further comprises at least one polyalcohol, selected from the group consisting of ethylene glycol, diethylene glycol, triethylene glycol, 1,2-propylene glycol, dipropylene glycol, tripropylene glycol, and glycerol.

8. The hydrogel of claim 7, wherein the hydrogel contains 0.01 to 40 wt. %, polyalcohol.

9. The hydrogel of claim 1, wherein the hydrogel further comprises 1 to 10 wt. % of a long-chain ester.

10. The hydrogel of claim 1 wherein the hydrogel further comprises 0.01 to 0.1 wt. % of perfume oils.

11. The method of claim 2, wherein the conjugate is present incorporated in an ointment or a cream.

12. The method of claim 2, wherein the conjugate is present in a hydrogel as a disinfectant cleaner.

13. A process for the production of the hydrogel of claim 7, wherein the hydrogel is produced from water and thickener and to this is added at a temperature of 20 to 60° C., first of all the polyalcohol and then the triiodomethane in the solubility promoter.

14. The process of claim 13 further comprising the step of homogenizing the hydrogel after the addition of the triiodomethane.

15. A process for preparing a conjugate comprising the step of separating said conjugate from the hydrogel of claim 7 by precipitation by means of high sodium chloride concentration or by high water dilution.

* * * * *

UNITED STATES PATENT AND TRADEMARK OFFICE
CERTIFICATE OF CORRECTION

PATENT NO.         : 6,958,157 B1                                             Page 1 of 1
APPLICATION NO. : 10/130940
DATED              : October 25, 2005
INVENTOR(S)        : Ulrich Doht It is certified that error appears in the above-identified patent and that said Letters Patent is hereby corrected as shown below:

Title Page;
Item (76) in the inventor's address, column should read

Ulrich Doht
        Heidschnuckenweg 32
        21224 Rosengarten
        Germany Signed and Sealed this Third Day of July, 2007

JON W. DUDAS
*Director of the United States Patent and Trademark Office*